(12) United States Patent
Rathjen et al.

(10) Patent No.: US 11,554,045 B2
(45) Date of Patent: *Jan. 17, 2023

(54) DEVICE FOR PROCESSING EYE TISSUE BY MEANS OF A PULSED LASER BEAM

(71) Applicant: SIE AG Surgical Instrument Engineering, Port (CH)

(72) Inventors: Christian Rathjen, Bremen (DE); Hartmut Kanngiesser, Zurich (CH); Vincent Ducry, Fribourg (CH); Lorenz Klauser, Meikirch (CH)

(73) Assignee: SIE AG Surgical Instrument Engineering, Port (CH)

( * ) Notice: Subject to any disclaimer, the term of this patent is extended or adjusted under 35 U.S.C. 154(b) by 378 days.

This patent is subject to a terminal disclaimer.

(21) Appl. No.: 16/941,639

(22) Filed: Jul. 29, 2020

(65) Prior Publication Data

US 2020/0352783 A1 Nov. 12, 2020

Related U.S. Application Data

(63) Continuation of application No. 15/645,538, filed on Jul. 10, 2017, now Pat. No. 10,758,414, which is a
(Continued)

(51) Int. Cl.
*A61F 9/00* (2006.01)
*A61F 9/008* (2006.01)

(52) U.S. Cl.
CPC .......... *A61F 9/008* (2013.01); *A61F 9/00825* (2013.01); *A61F 2009/00872* (2013.01); *A61F 2009/00897* (2013.01)

(58) Field of Classification Search
CPC .. A61B 3/0025; A61B 3/1025; A61B 1/00172
(Continued)

(56) References Cited

U.S. PATENT DOCUMENTS

| 4,781,455 A | 11/1988 | Maehler et al. |
| 5,274,492 A | 12/1993 | Razzaghi |

(Continued)

FOREIGN PATENT DOCUMENTS

| DE | 3724282 A1 | 2/1989 |
| EP | 1486185 A1 | 12/2004 |
| WO | 20080098381 A1 | 8/2008 |

*Primary Examiner* — Shirley X Jian
(74) *Attorney, Agent, or Firm* — Banner & Witcoff, Ltd.

(57) ABSTRACT

For processing eye tissue using a pulsed laser beam (L), an ophthalmological device includes a projection optical unit for the focused projection of the laser beam (L) into the eye tissue, and a scanner system upstream of the projection optical unit for the beam-deflecting scanning of the eye tissue with the laser beam (L) in a scanning movement (s') performed over a scanning angle along a scanning line(s). The projection optical unit is tilted about an axis of rotation (q) running perpendicularly to a plane defined by the scanning line(s) and the optical axis (o) of the projection optical unit, the tilting of the projection optical unit tilting the scanning line (s) in said plane. Tilting of the scanning line(s) enables a displacement—dependent on the scanning angle—of the focus of the laser pulses projected into the eye tissue without vertical displacement of the projection optical unit.

20 Claims, 8 Drawing Sheets

Related U.S. Application Data continuation of application No. 13/683,681, filed on Nov. 21, 2012, now Pat. No. 9,737,436.

(60) Provisional application No. 61/563,640, filed on Nov. 25, 2011.

(58) Field of Classification Search
USPC .......................................... 606/2–19, 88–94
See application file for complete search history.

(56) References Cited

U.S. PATENT DOCUMENTS

| | | |
|---|---|---|
| 7,621,637 B2 | 11/2009 | Rathjen et al. |
| 8,746,881 B2 | 6/2014 | Rathjen |
| 9,138,349 B2 | 9/2015 | Wolfel et al. |
| 9,566,190 B2 | 2/2017 | Rathjen et al. |
| 9,737,436 B2 | 8/2017 | Rathjen et al. |
| 9,849,033 B2 | 12/2017 | Schuele et al. |
| 2007/0010804 A1 | 1/2007 | Rathjen et al. |
| 2009/0093798 A1 | 4/2009 | Charles |
| 2012/0144277 A1 | 6/2012 | Lee et al. |
| 2012/0150156 A1 | 6/2012 | Wolfel et al. |
| 2012/0150157 A1 | 6/2012 | Wolfel et al. |
| 2019/0183678 A1* | 6/2019 | Rathjen .................. A61F 9/008 |

* cited by examiner

DEVICE FOR PROCESSING EYE TISSUE BY MEANS OF A PULSED LASER BEAM

CROSS REFERENCE TO RELATED APPLICATIONS

The present application is a continuation of U.S. application Ser. No. 15/645,538, filed Jul. 10, 2017, which is a continuation of U.S. application Ser. No. 13/683,681, filed Nov. 21, 2012, now U.S. Pat. No. 9,737,436, entitled "DEVICE FOR PROCESSING EYE TISSUE BY MEANS OF A PULSED LASER BEAM", which claims benefit of and priority to U.S. Provisional Patent Application Ser. No. 61/563,640, filed Nov. 25, 2011, entitled "DEVICE FOR PROCESSING EYE TISSUE BY MEANS OF A PULSED LASER BEAM", the entire contents of each of which are hereby incorporated by reference herein in their entirety.

TECHNICAL FIELD

The present disclosure relates to an ophthalmological device for processing eye tissue by means of a pulsed laser beam. The present disclosure relates, in particular, to an ophthalmological device comprising a projection optical unit for the focused projection of the laser beam into the eye tissue, and a scanner system disposed upstream of the projection optical unit and serving for the beam-deflecting scanning of the eye tissue with the laser beam.

BACKGROUND

For processing eye tissue by means of a laser beam, a processing region is scanned with laser pulses by the pulsed laser beam being deflected in one or two scanning directions by means of suitable scanner systems (deflection devices). The deflection of the light beams or of the laser pulses, for example femtosecond laser pulses, is generally performed by means of movable mirrors which are pivotable about one or two scanning axes, for example by means of galvanoscanners, piezoscanners, polygon scanners or resonance scanners.

U.S. Pat. No. 7,621,637 describes a device for processing eye tissue, said device having a base station with a laser source for generating laser pulses and a scanner arranged in the base station with movable deflection mirrors for deflecting the laser pulses in a scanning direction. The deflected laser pulses are transmitted via an optical transmission system from the base station to an application head, which moves over a working region in accordance with a scanning pattern by means of a mechanically moved projection optical unit. The deflection in the scanning direction, which is much faster compared with the mechanical movement, is superimposed in the application head onto the mechanical movement of the projection optical unit and thus onto the scanning pattern thereof. A fast scanner system in the base station enables a fine movement of the laser pulses (microscan), which is superimposed onto the scanning pattern of the movable projection optical unit that covers a large processing region, for example the entire eye.

Although the known systems make it possible to process simple scanning patterns, for example to cut a tissue flap, this generally being performed as a large area segment with a simple edge geometry, in the case of applications which involve not only making tissue cuts in a substantially horizontally oriented processing area on a common focal area, but also intending to make cuts with a vertical cut component over different focus heights, e.g. cuts that are vertical or run obliquely with respect to the horizontal, the vertical movement of the projection optical unit or at least parts thereof for a vertical variation of the focus and thus of the cut height proves to be too slow for making cuts with a vertical component, that is to say with a variable depth of focus during cutting.

SUMMARY

The disclosure proposes a device for processing eye tissue by means of a pulsed laser beam which does not have at least some of the disadvantages of the prior art. In particular, the present disclosure proposes a device for processing eye tissue by means of a pulsed laser beam focused by a projection optical unit which enables tissue cuts with a vertical cut component, without vertical displacements of the projection optical unit having to be performed for this purpose.

According to the present disclosure, these aims are achieved by means of the features of the independent claims. Further advantageous embodiments are additionally evident from the dependent claims and the description.

An ophthalmological device for processing eye tissue by means of a pulsed laser beam comprises a projection optical unit for the focused projection of the laser beam or of the laser pulses into the eye tissue, and a scanner system disposed upstream of the projection optical unit and serving for the beam-deflecting scanning of the eye tissue with the laser beam or the laser pulses in a scanning movement performed over a scanning angle along a scanning line.

The above mentioned aims are achieved by the present disclosure, in particular, by virtue of the fact that the projection optical unit can be tilted about an axis of rotation running perpendicularly to a plane defined by the scanning line and the optical axis of the projection optical unit.

Preferably, the projection optical unit can be tilted about the axis of rotation in order to tilt the scanning line about a defined tilting angle in the plane running through the optical axis of the projection optical unit and the scanning line.

The tilting of the scanning line enables a displacement—dependent on the scanning angle—of the focus of the laser pulses projected into the eye tissue without vertical displacement of the projection optical unit.

In one embodiment variant, the ophthalmological device comprises a further scanner system, which is designed to scan the eye tissue with the laser pulses along a processing line, wherein the scanning movement running along the scanning line is superimposed on the processing line, and the projection optical unit can be tilted about the axis of rotation for the targeted tilting of a cutting plane defined by the processing line and the scanning line.

In one embodiment variant, the ophthalmological device comprises an adjusting device for setting a tilting of the projection optical unit about the axis of rotation with a defined tilting angle.

In a further embodiment variant, the ophthalmological device comprises a contact body which can be placed onto the eye and is light-transmissive at least in places, and a tilting of the projection optical unit about the axis of rotation brings about a tilting of the optical axis of the projection optical unit with respect to a normal to the surface of the contact body.

In one embodiment variant, the ophthalmological device comprises a drive coupled to the projection optical unit and serving for tilting the projection optical unit about the axis of rotation.

In a further embodiment variant, the ophthalmological device comprises a control module coupled to the drive and serving for controlling the drive for a targeted tilting of the projection optical unit about the axis of rotation.

In one embodiment variant, the control module is designed to tilt the projection optical unit about the axis of rotation in such a way that the scanning line is tilted with a predefined tilting angle.

In a further embodiment variant, the control module is designed to tilt the projection optical unit about the axis of rotation in such a way that the scanning line is tilted with the predefined tilting angle in a plane defined by the scanning line and an optical axis of the projection optical unit.

In a further embodiment variant, the control module is designed, during the processing of the eye tissue, to determine a changed tilting angle and to tilt the projection optical unit about the axis of rotation in such a way that the scanning line is tilted with the changed tilting angle.

BRIEF DESCRIPTION OF THE DRAWINGS

An embodiment of the present disclosure is described below on the basis of an example. The example of the embodiment is illustrated by the following enclosed figures.

DETAILED DESCRIPTION

Figure 1:
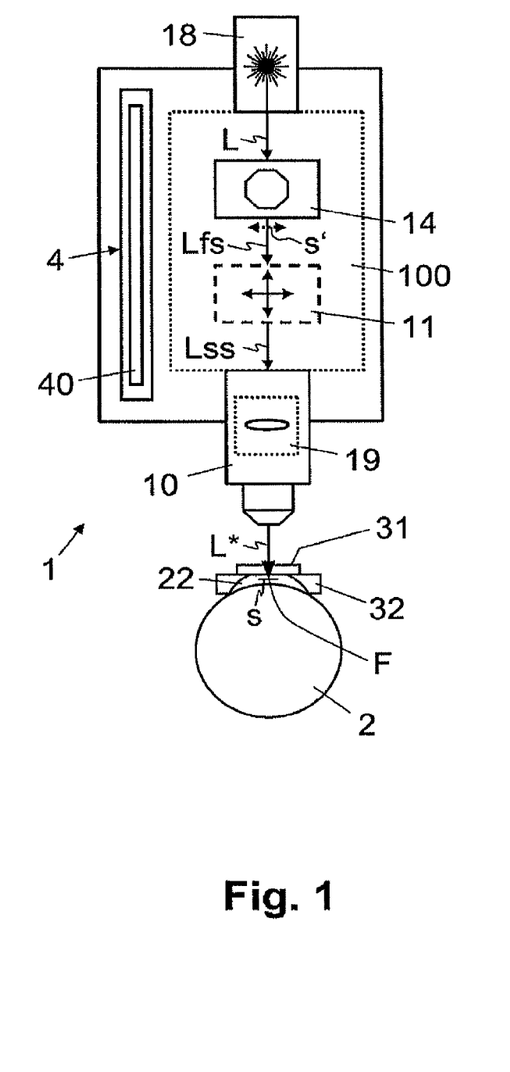
FIG. 1 shows a block diagram schematically illustrating an ophthalmological device for processing eye tissue with a pulsed laser beam, which device comprises a scanner system for scanning the eye tissue along a scanning line and a tilting system for tilting the scanning line.
Figure 1A:
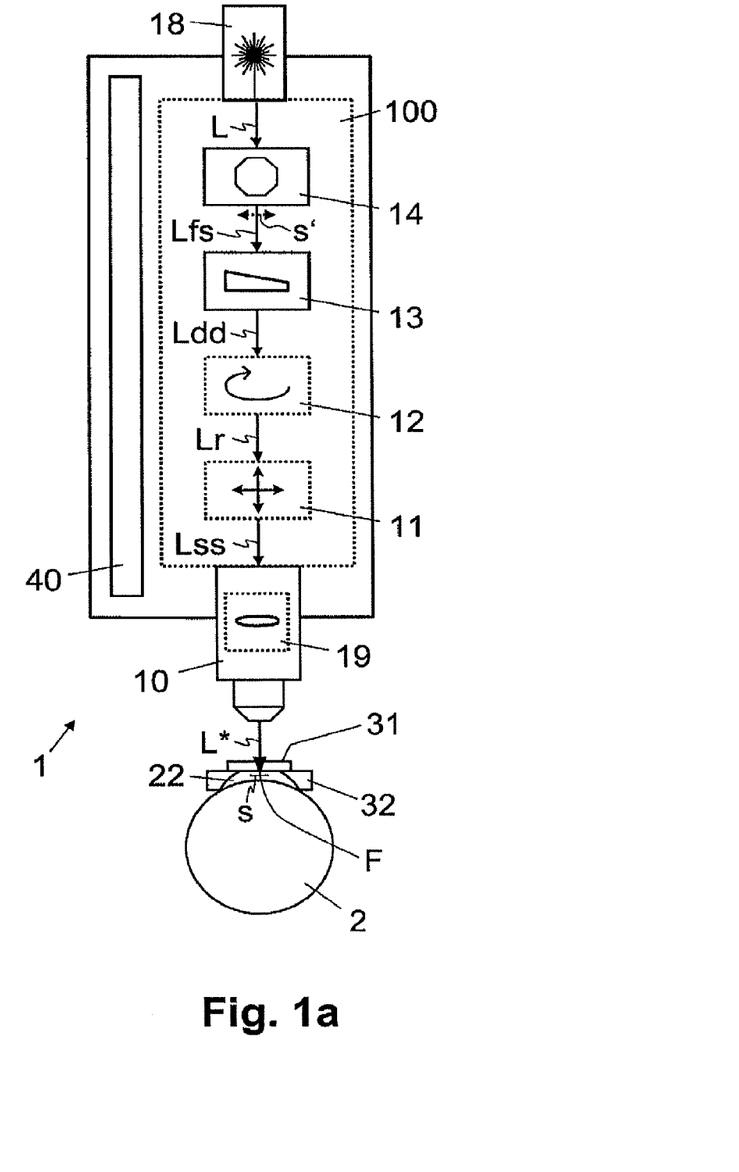
FIG. 1a shows a block diagram of the ophthalmological device in which, for the purpose of tilting the scanning line, at least one optical element is disposed upstream of the projection optical unit and generates in the beam path a laser beam divergence dependent on the scanning angle.
Figure 1B:
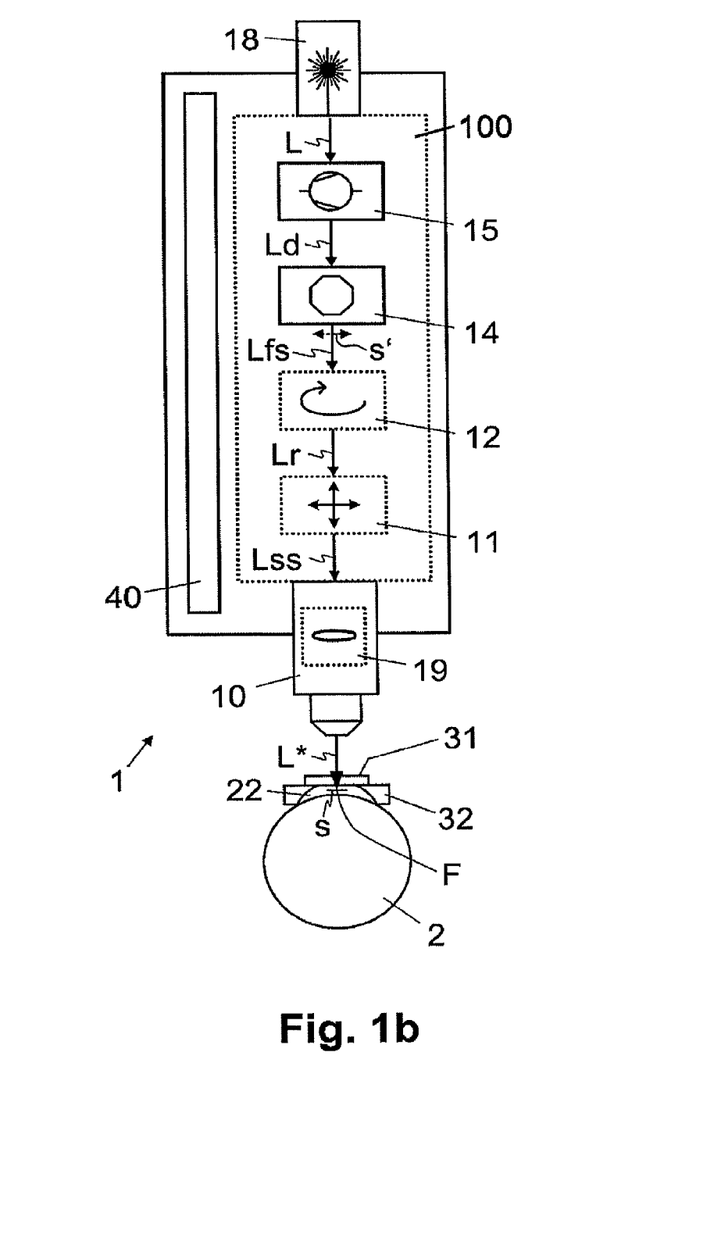
FIG. 1b shows a block diagram of the ophthalmological device in which, for the purpose of tilting the scanning line, a divergence modulator is disposed upstream of the scanner system and dynamically changes the divergence of the laser beam.

In FIGS. 1, 1a and 1b, the reference sign 1 in each case refers to an ophthalmological device for processing eye tissue by means of laser pulses, for example the cornea 22 or other tissue of an eye 2.

As is illustrated schematically in FIGS. 1, 1a and 1b, the ophthalmological device 1 comprises an optical transmission system 100 for transmitting laser pulses of a pulsed laser beam L supplied by a laser source 18 to a projection optical unit 10. The projection optical unit 10 is designed for the focused projection of the pulsed laser beam L or of the laser pulses for the punctiform tissue decomposition at a focus F (focal point) within the eye tissue. In FIGS. 1, 1a, 1b, 1d, 2a and 2b, the laser beam L projected by the projection optical unit 10 is designated by the reference sign L*.

The laser source 18 comprises, in particular, a femtosecond laser for generating femtosecond laser pulses having pulse widths of typically 10 fs to 1000 fs (1 fs=$10^{-15}$ s).

The laser source 18 is arranged in a separate housing or in a housing jointly with the projection optical unit 10.

It should be emphasized at this juncture that the reference sign L generally designates the pulsed laser beam L or the laser pulses thereof in the beam path from the laser source 18 as far as the focus F, but that depending on the context further reference signs are also used to designate the pulsed laser beam L or the laser pulses thereof at a specific location in the beam path or in the optical transmission system 100.

Figure 1C:
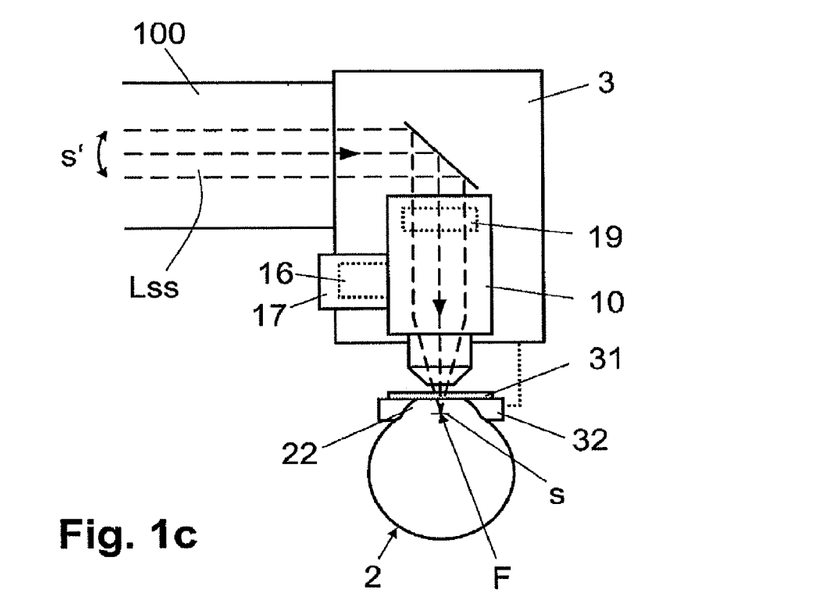
FIG. 1c shows a block diagram of an application head of the ophthalmological device, in which application head the projection optical unit can be tilted about an axis of rotation for the purpose of tilting the scanning line.

As is illustrated in FIG. 1c, the projection optical unit 10 is incorporated into an application head 3, for example, which can be placed onto the eye 2. The application head 3 is preferably placed onto the eye 2 via a contact body 31, which is light-transmissive at least in places, and fixed to the eye 2 by means of a vacuum-controlled suction ring 32, for example, wherein the contact body 31 and the suction ring 32 are connected to the application head 3 fixedly or removably. In one embodiment variant, the projection optical unit 10 comprises a focusing device 19 for setting the depth of focus, for example one or a plurality of movable lenses or a drive for moving the entire projection optical unit 10.

Figure 2A:
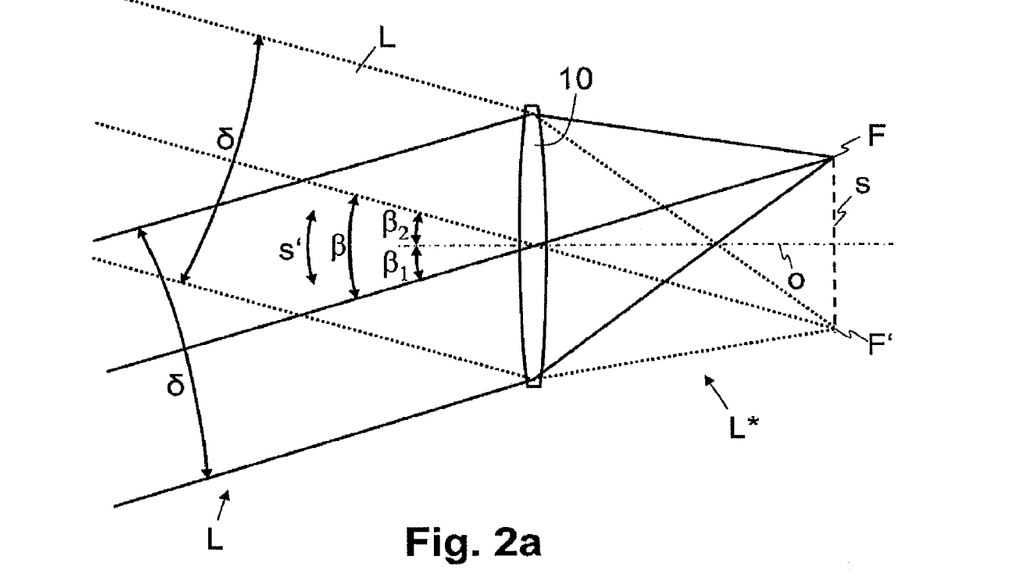
FIG. 2a shows a schematic cross section through a portion of the beam path which illustrates the scanning movement of the laser beam by a scanning angle and the resultant movement of the focus of the laser beam along the scanning line.

As can be seen in FIGS. 1, 1a and 1b, the ophthalmological device 1 comprises at least one scanner system 14 disposed upstream of the projection optical unit 10 and serving for scanning the eye tissue along a scanning line s. The scanner system 14 is designed to deflect the pulsed laser beam L or the laser pulses in order to scan the eye tissue in a processing fashion. The scanner system 14 comprises one or a plurality of movable deflection mirrors, for example a rotating polygon mirror (polygon scanner), and enables beam-deflecting scanning of the eye tissue with the pulsed laser beam L in a scanning movement s' performed over a scanning angle β along a scanning line s, as is illustrated in FIG. 2a. By means of the scanning movement s', the focus F of the projected laser beam L* is moved along the scanning line s, for example proceeding from the position of the focus F in the case of a deflection of the laser beam L with the scanning angle $β_1$ to the position of the focus F' in the case of a deflection of the laser beam L with the scanning angle $β_2$.

The beam-deflecting scanner system 14 is embodied as a resonant, oscillating, or freely addressable scanner depending on the operating mode and/or construction and comprises, for example, a galvanoscanner, a piezo-driven scanner, an MEM (microelectro-mechanical scanner), an AOM (acousto-optical modulator) scanner or an EOM (electro-optical modulators) scanner.

As is illustrated in FIGS. 1a and 1b, in one embodiment variant the ophthalmological device 1 comprises a rotation element 12, which is arranged in the beam path and is disposed downstream of the scanner system 14 and serves for rotating a scanning plane defined by the scanning movement s' and the optical transmission axis about the optical transmission axis, for example a K-mirror. In FIGS. 1a and 1b, the laser beam L with the scanning plane rotated by the rotation element 12 is designated by the reference sign Lr.

In one embodiment variant, the ophthalmological device 1 comprises a further, optional scanner system 11 disposed upstream of the projection optical unit 10 and downstream of the scanner system 14. The scanner system 11 is designed to scan the eye tissue with the pulsed laser beam L or the laser pulses along a processing line b, as is illustrated by way of example in the plan view in FIG. 4a. A meandering processing line b is illustrated in the example in FIG. 4a; the person skilled in the art will understand that the processing line b, depending on the application and driving of the scanner system 11, can also assume other line shapes, for example spiral, circular, or a freeform shape extending over a part or all of the region B of the eye tissue that is to be processed. The scanner system 11 is embodied as a mechanical scanner that moves the projection optical unit 10 over the entire processing region B along the processing line b by means of one or a plurality of movement drivers, or the scanner system 11 is embodied in a beam-deflecting fashion, for example as a galvanoscanner, and comprises one or two deflection mirrors—movable about respectively one or two axes—for deflecting the pulsed laser beam L or the laser pulses over the entire processing region B along the processing line b.

The scanner system 14 disposed upstream of the scanner system 11 has a scanning speed that is a multiple of the scanning speed of the scanner system 11. Accordingly, the scanner system 14 can also be designated as a fast scan system that generates the deflected laser beam Lfs, and the scanner system 11 can be designated as a slow scan system that generates the deflected laser beam Lss. The two scanner systems 11, 14 are designed and coupled such that the scanning movement s' running along the scanning line s is superimposed on the processing line b, as is illustrated schematically and by way of example in the x/y plan view in FIG. 4a. As the scanning line s defines a cutting line in the case of a single scanner system 14 having a single scanning axis, a cutting area is thus defined by the superimposition of the scanning line s onto the processing line b.

Figure 1D:
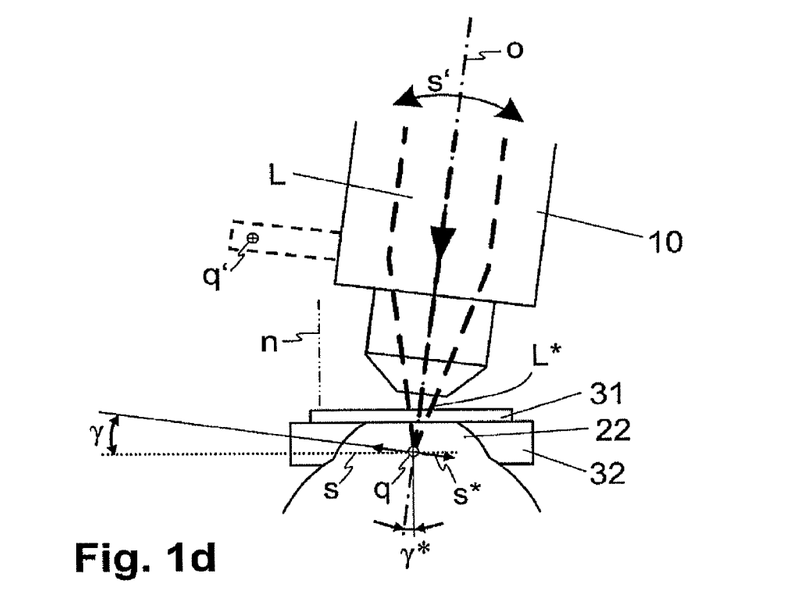
FIG. 1d shows a block diagram illustrating the projection optical unit and correspondingly the scanning line in a tilted state.
Figure 2B:
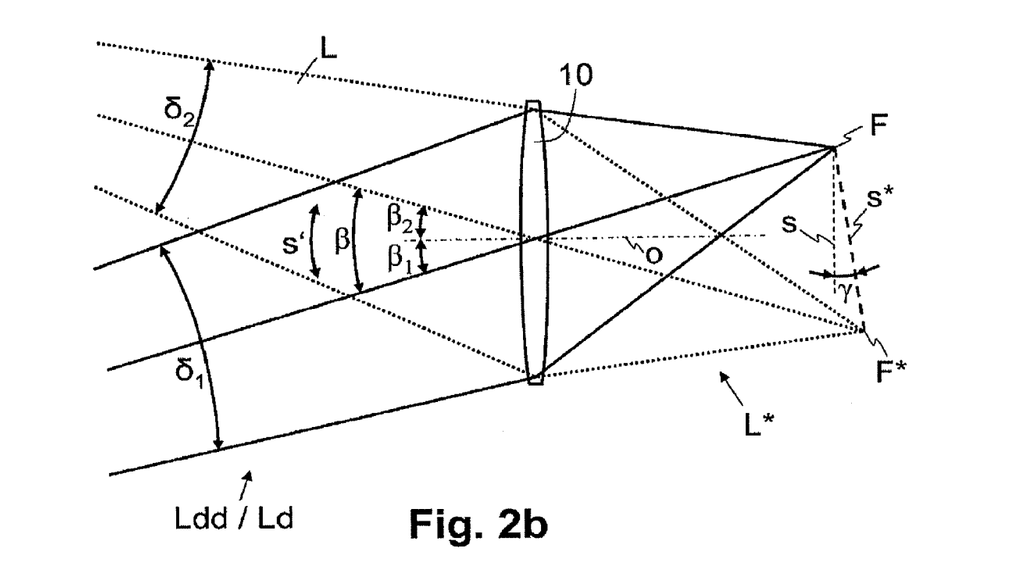
FIG. 2b shows the schematic cross section of the beam path portion in the case of a variation of the divergence of the laser beam depending on the scanning angle, and the resultant tilting of the scanning line by a tilting angle.

As is illustrated schematically in FIG. 1, the ophthalmological device 1 furthermore comprises a tilting system 4 for tilting the scanning line s or the cutting area. As can be seen in FIGS. 1d and 2b, the tilted scanning line s* is tilted by the tilting angle γ relative to the scanning line s in a plane running through the optical axis o of the projection optical unit 10 and of the scanning line s. Accordingly, the tilting system 4 also enables a tilting of the cutting area defined by the scanning line s and processing line b by the tilting angle γ, for example—depending on the application and control—a tilting of the entire cutting area or of individual paths defined by the processing line b.

Figure 4A:
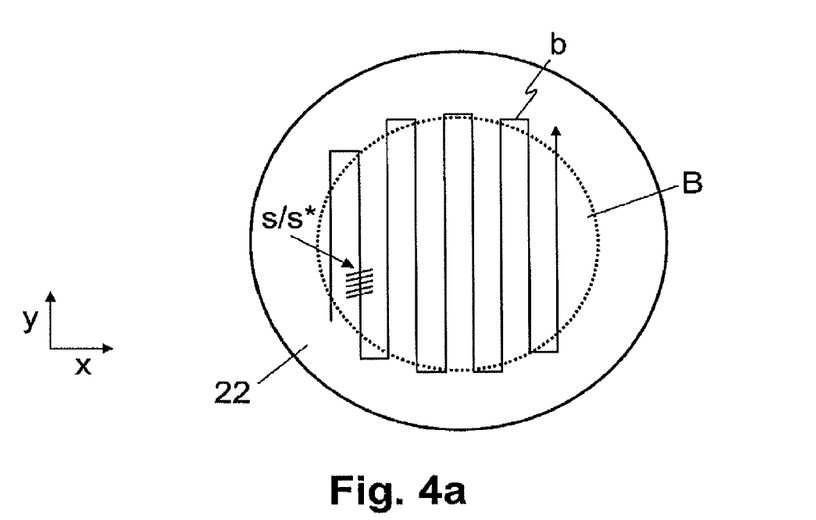
FIG. 4a shows in the plan view of the cornea, the superimposition of the scanning movement onto a processing line for processing the eye tissue in an extended processing region.
Figure 4B:
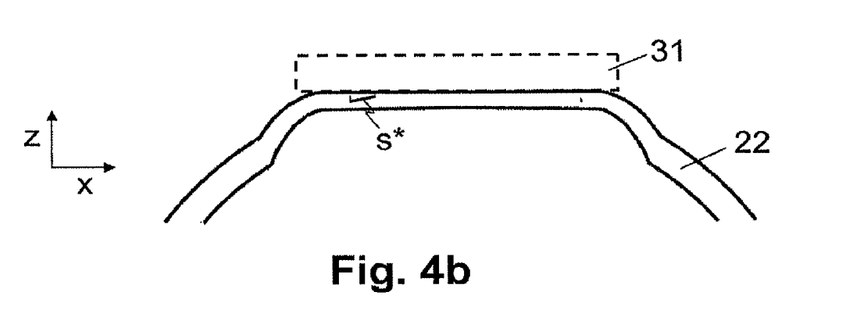
FIG. 4b shows, in the cross section of the cornea, the tilted scanning line along which the eye tissue is scanned and processed by the pulsed laser beam.
Figure 4C:
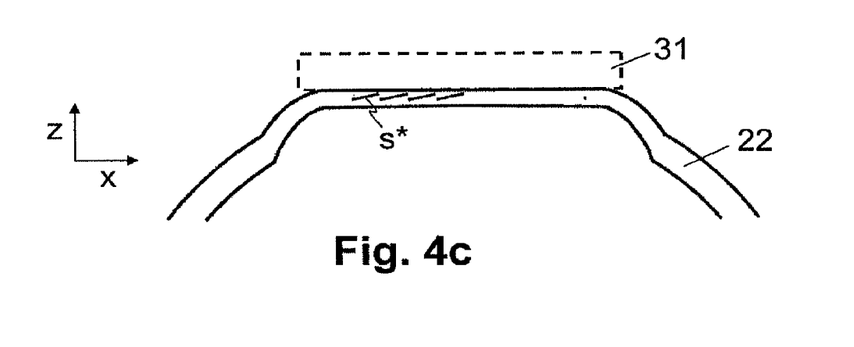
FIG. 4c shows, in the cross section of the cornea, the tilted scanning lines of a plurality of processing paths along which the eye tissue is scanned and processed by the pulsed laser beam.

In the example in FIG. 4a, the scanning movement s' running along the scanning line s or the tilted scanning line s* is superimposed on the meandering processing line b and thus generates a cutting area extended over the processing region B when moving over the entire processing line b. FIGS. 4b and 4c show the cross-sectional illustrations—corresponding to FIG. 4a—of the cornea 22 applanated by means of the contact body 31 after moving over a path or four successive paths of the processing line b with a scanning movement s' along the tilted scanning line s*. The tilted scanning line s* of the exemplary application illustrated in FIGS. 4a, 4b, 4c enables the correction or removal of residual errors in mutually adjacent processing paths which arise when the optical axis o of the projection optical unit 10 is not oriented perpendicularly to the applanation area of the contact body 31.

Figures 5, 5A:
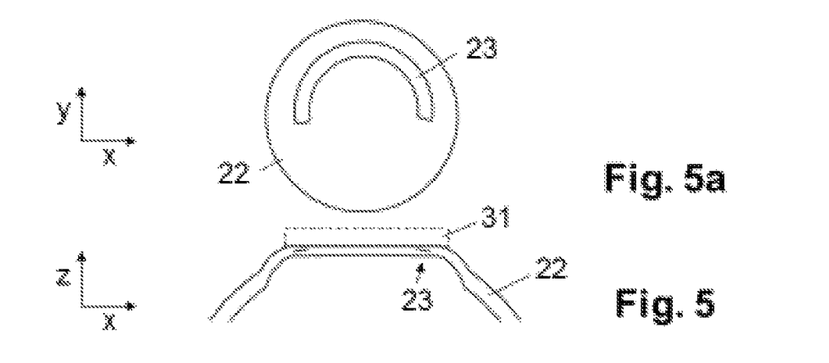
FIG. 5a shows, in the plan view of the cornea, an exemplary application of a circle-arc-shaped conic path cut.
FIG. 5 shows the cross section of the cornea, illustrating that the circle-arc-shaped conic path cut is based on a tilted scanning line that is moved along a circle-arc-shaped processing line.

The exemplary application in FIGS. 5, 5a show, in FIG. 5a, a plan view of the cornea 22 and a schematically illustrated conic path cut 23 made therein, the cross section of which is illustrated in FIG. 5. The conic path cut 23 is produced by the superimposition of a scanning movement s' performed along a tilted scanning line s* onto a circle-arc-shaped processing line b, wherein the tilted scanning line s* is oriented for example perpendicularly to the processing line b.

Figures 6, 6A:
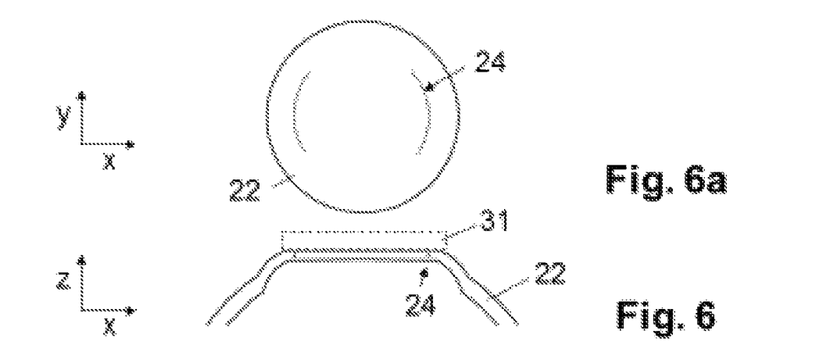
FIG. 6a shows in the plan view of the cornea, an exemplary application of two circle-arc-shaped vertical cuts.
FIG. 6 shows the cross section of the cornea, illustrating that the two circle-arc-shaped vertical cuts are in each case based on a tilted scanning line that is moved along the relevant processing line, in a manner oriented in the direction of a circle-arc-shaped processing line.

The exemplary application in FIGS. 6, 6a show, in FIG. 6a, a plan view of the cornea 22 and two schematically illustrated circle-arc-shaped vertical cuts 24 made therein, a cross section of which is illustrated in FIG. 6. The two vertical cuts 24 are in each case produced by the superimposition of a scanning movement s' performed along a tilted scanning line s* onto a circle-arc-shaped processing line b, wherein the tilted scanning line s* is additionally oriented in the direction of the relevant processing line b.

Figure 7:
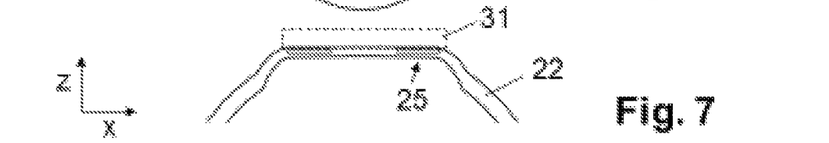
FIG. 7 shows the cross section of the cornea, illustrating that the plurality of vertical cuts is in each case based on a tilted scanning line that is moved along the relevant processing line, in a manner oriented in the direction of a processing line oriented toward the center.
Figure 7A:
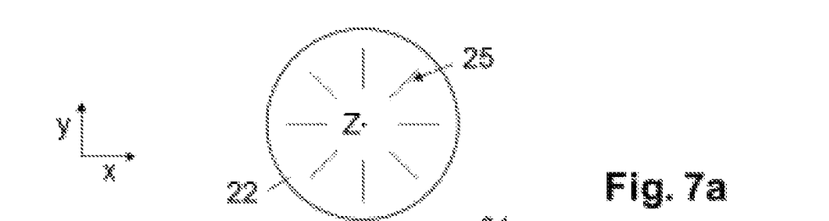
FIG. 7a shows in the plan view of the cornea, an exemplary application of a plurality of vertical cuts which are oriented toward a common center.

The exemplary application in FIGS. 7, 7a show, in FIG. 7a, a plan view of the cornea 22 and a plurality of schematically illustrated vertical cuts 25 made therein, which are oriented rectilinearly toward a center point Z (vertex) of the cornea 22 and a cross section of which is illustrated in FIG. 6. The vertical cuts 25 are in each case produced by the superimposition of a scanning movement s' performed along a tilted scanning line s* onto a rectilinear processing line b oriented toward the center point Z (vertex) of the cornea 22, wherein the tilted scanning line s* is additionally oriented in each case in the direction of the relevant processing line b.

In order to control the tilting of the scanning line s or the cutting area, the tilting system 4 comprises a control module 40, which is designed to control components of the tilting system 4 in such a way that the scanning line s (and thus, if appropriate, also the cutting area) is tilted by a predefined tilting angle γ in a plane running through the optical axis o of the projection optical unit 10 and the scanning line s. The tilting angle γ is fixedly defined, for example, is input via a user interface or is constantly changed by a control function of the control module 40 during the processing of the eye tissue. The control module 40 comprises a programmable control device, for example one or a plurality of processors with program and data memory and programmed software modules for controlling the processors.

Depending on the embodiment variant, the tilting system 4 comprises different components which are provided for tilting the scanning line s and are connected to the control module 40 for control purposes.

FIG. 1a illustrates an ophthalmological device 1, in which the tilting system 4 comprises one or a plurality of optical elements 13 which, disposed upstream of the projection optical unit 10, are arranged in the beam path from the scanner system 14 to the projection optical unit 10 and which are designed to generate in the beam path a divergence δ, $δ_1$, $δ_2$ of the laser beam L, said divergence being dependent on the scanning angle β, $β_1$, $β_2$ (see FIG. 2b).

As is illustrated in FIG. 1a, the optical element 13 is disposed downstream of the scanner system 14 and varies the divergence δ, $δ_1$, $δ_2$ of the laser beam L depending on the scanning angle β, $β_1$, $β_2$ of the laser beam L deflected by the scanner system 14. The laser beam L with the divergence δ, $δ_1$, $δ_2$ varied by the optical element 13 depending on the scanning angle β, $β_1$, $β_2$ is designated by the reference sign Ldd in FIGS. 1a and 2b. In the embodiment variant with the optional rotation element 12, the optical elements 13 or the optical element 13 are/is disposed upstream of the rotation element 12 in the beam path.

As is illustrated in FIG. 2a, the laser beam L in the absence of the optical element 13 has in each case an unchanged, constant divergence δ for different scanning angles β, $β_1$, $β_2$. A divergence δ of approximately zero is often set. With the optical element 13 present, however, the laser beam L has a different divergence $δ_1$, $δ_2$ for different scanning angles β, $β_1$, $β_2$, as illustrated in FIG. 2b. As can be seen in FIG. 2b, the optical element 13 is designed such that it varies the divergence δ, $δ_1$, $δ_2$ of the laser beam L depending on the scanning angle β, $β_1$, $β_2$ such that the focus F, F* of the projected laser beam is displaced depending on the scanning angle β, $β_1$, $β_2$ in the projection direction, thus resulting in a tilted scanning line s* which is tilted from the untilted scanning line s by the tilting angle γ in the plane formed by the optical axis o of the projection optical unit 10 and of the scanning line S. When the scanning line s is tilted, the eye tissue is scanned in a beam-deflecting manner along the tilted scanning line s* by the scanner system 14 with the pulsed laser beam L in a scanning movement s' performed over the scanning angle β, as is illustrated in FIG. 2b. In this case, the focus F of the projected laser beam L* is moved by the scanning movement s' along the tilted scanning line s*, for example proceeding from the position of the focus F in the case of a deflection of the laser beam L with the scanning angle $β_1$ toward the position of the focus F* in the case of a deflection of the laser beam L with the scanning angle $β_2$.

Embodiments of the optical elements 13 or of the optical element 13 comprise, for example, wedge plates, prisms, lenses, diffractive optical elements and aspherical mirrors.

In an alternative embodiment variant, the optical element 13 is arranged directly in the scanner system 14 and configured, for example, as a deflection mirror having a variable surface curvature.

In order to set the divergence δ, $δ_1$, $δ_2$ of the laser beam L depending on the scanning angle β, $β_1$, $β_2$ the optical elements 13 or the optical element 13 can be introduced into the beam path or withdrawn from the beam path. As an alternative or in addition, the optical elements 13 or the optical element 13 can be set or adjusted for the purpose of setting the divergence δ, $δ_1$, $δ_2$ of the laser beam L depending on the scanning angle β, $β_1$, $β_2$, for example by rotation of the optical elements 13 about the optical axis o, by tilting of the optical elements 13 about an axis of rotation, or by displacement of the optical elements 13 along a translation axis tilted relative to the optical axis o.

In the embodiment variant with the optional scanner system 11, which scans the eye tissue with the laser beam L or the laser pulses along a processing line b on which the scanning movement s' of the scanner system 14 disposed upstream is superimposed, the optical elements 13 are designed to generate the divergence δ, $δ_1$, $δ_2$ of the laser beam L depending on the scanning angle β, $β_1$, $β_2$ for a targeted tilting of a cutting area defined by the scanning line s and the processing line b.

The control module 40 is designed to set the optical elements 13 or the optical element 13 such that the divergence δ, $δ_1$, $δ_2$ of the laser beam L depending on the scanning angle β, $β_1$, $β_2$ brings about a tilting of the scanning line s or of the cutting area defined by the scanning line s and the processing line b by the predefined tilting angle γ. For this purpose, the control module 40 comprises a control function which, for tilting angles γ that are predefined or constantly calculated anew during the processing of the eye tissue, determines respectively assigned control values for setting the optical elements 13, for example control values for setting an angle of rotation of the optical elements 13 about the optical axis o, a degree of tilting of the optical elements 13 about an axis of rotation or a position of the optical elements 13 on a translation axis tilted relative to the optical axis o, thereby defining the relative position of the optical elements 13 in the beam cross section, or a surface curvature of the optical elements 13.

FIG. 1b illustrates an ophthalmological device 1 in which the tilting system 4 comprises a divergence modulator 15, which is disposed upstream of the scanner system 14 and which is designed to dynamically vary the divergence δ of the laser beam L.

Figure 3:
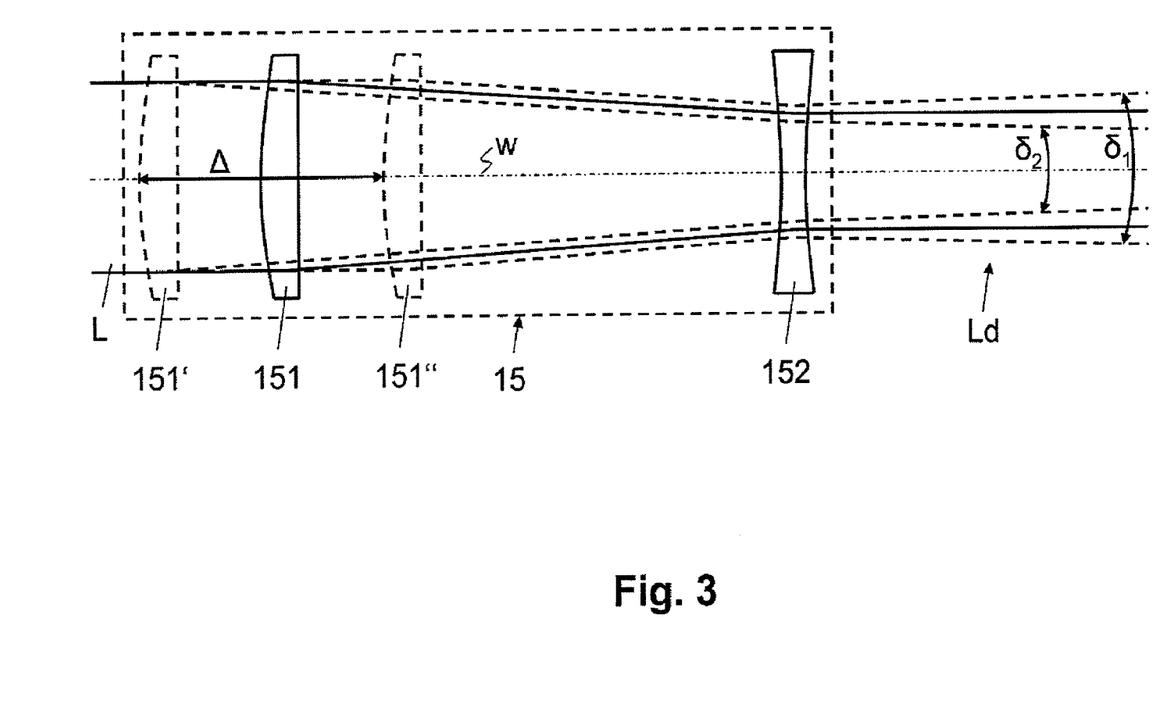
FIG. 3 shows a schematic cross section of a portion of the beam path in a divergence modulator with at least one displaceable lens and illustrates the laser beam divergence varied by the displacement of the lens.

FIG. 3 schematically illustrates an embodiment variant of the divergence modulator 15 having two serially arranged optical lenses 151, 152, at least one of which is displaceable for modulating the divergence δ of the laser beam L on an optical transmission axis w. For dynamically modulating the divergence δ of the laser beam L, the movable lens 151 is coupled to a movement driver. As can be seen in the example in FIG. 3, in the case of a first basic position 151' of the movable lens, the laser beam L has a corresponding divergence $δ_1$. In the case of a displacement of the movable lens 151 on the transmission axis w, the divergence of the laser beam L varies continuously and has a changed divergence $δ_2$ in the case of the position 151" displaced by the excursion distance Δ. The laser beam L with the divergence δ, $δ_1$, $δ_2$ modulated by the divergence modulator 15 is designated by the reference sign Ld in FIGS. 1b, 2b and 3.

In alternative embodiments, the divergence modulator 15 comprises a spatial light modulator for modulating the wavefront of the laser beam L, a surface light modulator for modulating the reflection angles at a plurality of points of a reflection surface over which the laser beam L is guided, a refraction modulator for modulating the refractive index of an optical element at a plurality of points in the cross section of the beam path, and/or an amplitude modulator for amplitude modulation at a plurality of points in the cross section of the beam path, that is to say in the beam profile, of the laser beam L.

The divergence modulator 15 is designed to modulate the divergence $\delta$, $\delta_1$, $\delta_2$ of the laser beam L (during the scanning movement s') with a frequency or speed of at least the same magnitude as that with which the scanner system 14 performs the scanning movement s' over the scanning angle $\beta$. Moreover, the divergence modulator 15 is coupled to the scanner system 14 such that the variation of the divergence $\delta$, $\delta_1$, $\delta_2$ of the laser beam L is synchronized with the scanning angle $\beta$, $\beta_1$, $\beta_2$ of the scanning movement s'. As is illustrated schematically in FIG. 2b, this results in a divergence $\delta$, $\delta_1$, $\delta_2$ of the laser beam L which varies with the scanning angle $\beta$, $\beta_1$, $\beta_2$ i.e. is dependent on the scanning angle $\beta$, $\beta_1$, $\beta_2$.

The divergence modulator 15 can be set and controlled by the control module 40 with regard to modulation frequency or modulation speed and modulation depth or modulation intensity, e.g. the excursion distance $\Delta$ in the embodiment according to FIG. 3. The modulation frequency of the divergence modulator 15 is synchronized for example with the scanning speed of the scanner system 14, e.g. a displacement over the excursion distance $\Delta$ is carried out during a scanning movement s' over the scanning angle $\beta$ (e.g. from $\beta_1$ to $\beta_2$).

As has already been described above in connection with the optical element 13, in the case of a divergence $\delta$, $\delta_1$, $\delta_2$ of the laser beam L that is varied depending on the scanning angle $\beta$, $\beta_1$, $\beta_2$, a displacement of the focus F, F* of the projected laser beam L*, said displacement being dependent on the scanning angle $\beta$, $\beta_1$, $\beta_2$, arises, as is illustrated by way of example in FIG. 2b. In the case of corresponding synchronization of the variation of the divergence $\delta$, $\delta_1$, $\delta_2$ of the laser beam L with the scanning angle $\beta$, $\beta_1$, $\beta_2$ of the scanning movement s', a tilting of the scanning line s results. The tilting angle $\gamma$ between the tilted scanning line s* and the untilted scanning line s in the plane formed by the optical axis o of the projection optical unit 10 and of the scanning line s can be adjusted by the modulation depth or modulation intensity, e.g. by the excursion distance $\Delta$.

If the divergence modulator 15 is designed to modulate the divergence $\delta$, $\delta_1$, $\delta_2$ of the laser beam L with a greater frequency or speed than the scanner system 14 performs the scanning movement s', this does not make it possible to tilt the scanning line s merely by the tilting angle $\gamma$, but rather to deform the scanning line s in the plane formed by the optical axis o of the projection optical unit 10 and of the untilted scanning line s, wherein, in the case of a varying modulation speed, a "nonlinear tilting" and thus a deformation of the scanning line s in the projection direction are also made possible.

In the embodiment variant with the optional scanner system 11, which scans the eye tissue with the laser beam L or the laser pulses along a processing line b on which the scanning movement s' of the upstream scanner system 14 is superimposed, the divergence modulator 15 enables a divergence $\delta$, $\delta_1$, $\delta_2$ of the laser beam L depending on the scanning angle $\beta$, $\beta_1$, $\beta_2$ for a targeted tilting of the cutting area defined by the scanning line s and the processing line b. At a modulation speed of the divergence modulator 15 which is higher than the scanning speed of the scanning system 14, the divergence modulator 15 enables a targeted deformation of said cutting area.

The control module 40 is designed to set the divergence modulator 15 such that the divergence $\delta$, $\delta_1$, $\delta_2$ of the laser beam L depending on the scanning angle $\beta$, $\beta_1$, $\beta_2$ brings about a tilting of the scanning line s or of the cutting area defined by the scanning line s and the processing line b by the predefined tilting angle $\gamma$. For this purpose, the control module 40 comprises a control function which, for tilting angles $\gamma$ that are predefined or constantly calculated anew during the processing of the eye tissue, determines respectively assigned control values for setting the divergence modulator 15, in particular for setting the modulation depth or modulation intensity, e.g. the excursion distance $\Delta$, and the modulation speed, wherein the synchronization between the scanner system 14 and the divergence modulator 15 is preferably effected via common synchronization lines or synchronization signals. For a targeted deformation of the cutting area defined by the scanning line s and the processing line b at a correspondingly high modulation speed of the divergence modulator 15, the control module 40 controls the divergence modulator 15 with dynamically changing control values for a modulation depth or modulation intensity, e.g. the excursion distance $\Delta$, and/or modulation speed varying during the scanning movement s'.

In an embodiment variant in accordance with FIG. 1b, the ophthalmological device 1 merely comprises one scanner system 14 or 11, for example a galvanoscanner system, which is disposed between the divergence modulator 15 and the projection optical unit 10 and which is designed to scan the eye tissue two-dimensionally, that is to say both in a first scanning direction x and in a second scanning direction y perpendicular thereto (see FIG. 4a), in a processing fashion along a scanning line s or processing line b. The control module 40 is designed to control the scanner system 14 or 11 for the processing of the eye tissue along different scanning lines s or processing lines b which have, for example, a meandering, spiral, circular or freeform shape and extend over a part or all of the region B of the eye tissue that is to be processed. The control module 40 is additionally designed to control processing depth in the z-direction, which is perpendicular to the first scanning direction x and second scanning direction y, by corresponding setting of the divergence modulator 15. The processing depth in the z-direction can thus be modulated by corresponding driving of the divergence modulator 15 by the control module 40 during the processing of the eye tissue in the scanning directions x, y along the scanning line s or processing line b. As a result, not only planar but also curved cutting areas are possible in the eye tissue, in particular cutting areas shaped in a targeted manner, for example parts of sphere surfaces, ellipsoid surfaces, one-dimensionally or two-dimensionally undulatory shapes or other freeform areas, without the projection optical unit 10 or optical components thereof having to be moved for this purpose. In this case, both the depth adjustment range in the eye tissue that is made possible by the variable setting of the modulation depth or modulation intensity of the divergence modulator 15 in the z-direction, and the excursion range of the requisite excursion distance $\Delta$ of the lens 151 are significantly smaller than the thickness of the cornea 22, of the lens or of other tissue parts of the eye. Consequently, in the eye tissue a modulation of the processing depth in the z-direction is possible with a significantly higher frequency than would be possible by moving the large mass of the projection optical unit 10 or optical components thereof.

FIG. 1c illustrates an ophthalmological device 1 in which the tilting system 4 is based on the projection optical unit 10, which is configured such that it can be tilted about an axis of rotation q (or q') running perpendicularly to its optical axis o and to the scanning line s. As is indicated with the axis of rotation q', the axis of rotation q' need not run directly through the optical axis o and the scanning line s; it suffices if the axis of rotation q, q' runs perpendicularly to a plane defined by the scanning line s and the optical axis o.

As is illustrated in FIG. 1d, a tilting of the projection optical unit 10 about the axis of rotation q, q' with the rotation angle γ* brings about a tilting of the scanning line s by the tilting angle γ=γ*. In the example in FIG. 1d, the tilted scanning line s* in the plane defined by the scanning line s and the optical axis of the projection optical unit is tilted relative to the untilted scanning line s by the same tilting angle γ as the optical axis o of the projection optical unit 10 relative to a normal n to the surface with respect to the contact body 31. However, the tilting angle γ and the rotation angle γ* can also be different, if e.g. the object- and image-side refractive indices of the projection optical unit 10 are different.

In the embodiment variant with the optional scanner system 11, which scans the eye tissue with the laser beam L or the laser pulses along a processing line b on which the scanning movement s' of the upstream scanner system 14 is superimposed, the projection optical unit 10 that can be tilted about the axis of rotation q, q' enables a corresponding tilting of the cutting area defined by the scanning line s and the processing line b.

For setting and fixing the tilting of the projection optical unit 10 and the resulting tilting of the scanning line s or cutting area, the ophthalmological device 1 in one embodiment variant comprises an adjusting device 16 coupled to the projection optical unit 10.

For the automated tilting of the projection optical unit 10, the ophthalmological device 1 in a further embodiment variant comprises a drive 17 coupled to the projection optical unit 10. Moreover, the control module 40 is connected to the drive 17 for the purpose of controlling the tilting of the projection optical unit 10 and the resultant tilting of the scanning line s or of the cutting area in accordance with a tilting angle γ that is predefined or is constantly calculated anew during the processing of the eye tissue.

We claim:

1. An ophthalmological device for processing eye tissue by means of a pulsed laser beam, comprising:
    a projection optical unit configured for projection of the pulsed laser beam in a projection direction onto a focus in the eye tissue;
    a first scanner system configured to scan the eye tissue with the pulsed laser beam in an x-scanning direction and in a y-scanning direction, perpendicular to the x-scanning direction, to scan the eye tissue with the pulsed laser beam along a processing line transverse to the projection direction;
    an optical system with an optical transmission axis, configured to generate a varying divergence of the laser beam, such that the focus is displaced in the projection direction;
    a second scanner system disposed upstream of the first scanner system and configured for beam-deflecting scanning of the eye tissue with the pulsed laser beam in a scanning movement along a scanning line transverse to the optical transmission axis and superimposed on the processing line;
    wherein the ophthalmological device further comprises:
    a rotation element arranged downstream of the optical system and configured to rotate about the optical transmission axis a scanning plane defined by the optical transmission axis and the scanning movement of the second scanner system.

2. The ophthalmological device of claim 1, wherein the first scanner system is configured to scan the eye tissue with the pulsed laser beam in an x-scanning direction x and in a y-scanning direction perpendicular to the x-scanning direction, the second scanner is configured to scan the eye tissue with the pulsed laser beam with a faster scanning speed than the first scanner, and
    the optical system is configured to generate the varying divergence of the pulsed laser beam for defining the processing depth in a z-direction perpendicular to the x-scanning direction and the y-scanning direction.

3. The ophthalmological device of claim 2, further comprising a control module configured to control the optical system to modulate the processing depth in the z-direction during the processing of the eye tissue in the x-scanning direction and y-scanning direction.

4. The ophthalmological device of claim 2, further comprising a control module configured to control the optical system to modulate the processing depth in the z-direction during the processing of the eye tissue in the x-scanning direction and y-scanning direction so as to generate a curved cutting area in the eye tissue with at least one shape from the following list: a spherical surface, an ellipsoid surface, a one-dimensionally undulatory shape, a two-dimensionally undulatory shape, and a freeform shaped area.

5. The ophthalmological device of claim 1, wherein the optical system is coupled to the second scanner system such that the varying divergence of the pulsed laser beam is synchronized with the scanning movement by the second scanner system.

6. The ophthalmological device of claim 1, wherein the first scanner system is configured for beam-deflecting scanning along the processing line having a line shape of at least one of the following list: a meandering shape, a spiral shape, and a circular shape.

7. The ophthalmological device of claim 1, wherein the optical system is configured to generate the varying divergence of the pulsed laser beam for a targeted curvature of a cutting area defined by the processing line and the scanning line.

8. The ophthalmological device of claim 1, wherein the optical system is configured to generate the varying divergence of the pulsed laser beam faster than the scanning movement of the second scanner system along the scanning line so as to deform the scanning line in the projection direction.

9. The ophthalmological device of claim 1, wherein the optical system is configured to generate the varying divergence of the pulsed laser beam for a targeted tilting of the scanning line to produce a vertical cut in the eye tissue along the processing line.

10. The ophthalmological device of claim 1, wherein the first scanner system is configured to scan the eye tissue with the pulsed laser beam along a circle-arc-shaped processing line,
    the second scanner system is configured to scan the eye tissue with the pulsed laser beam in a scanning movement along a scanning line oriented perpendicularly to the circle-arc-shaped processing line, and the optical system is configured to generate the varying divergence of the pulsed laser beam for a targeted tilting of the scanning line to produce a conic path cut in the eye tissue.

11. The ophthalmological device of claim 1, wherein the first scanner system is configured to scan the eye tissue with the pulsed laser beam along a circle-arc-shaped processing line,
the second scanner system is configured to scan the eye tissue with the pulsed laser beam in a scanning movement along a scanning line oriented in direction of the circle-arc-shaped processing line, and
the optical system is configured to generate the varying divergence of the pulsed laser beam for a targeted tilting of the scanning line to produce a circle-arc-shaped vertical cut in the eye tissue.

12. The ophthalmological device of claim 1, wherein the first scanner system is configured to scan the eye tissue with the pulsed laser beam along rectilinear processing lines oriented toward a vertex of a cornea,
the second scanner system is configured to scan the eye tissue with the pulsed laser beam in a scanning movement along a scanning line oriented in direction of the respective processing line, and
the optical system is configured to generate the varying divergence of the pulsed laser beam for a targeted tilting of the scanning line to produce a plurality of vertical cuts oriented rectilinearly toward the vertex of the cornea.

13. The ophthalmological device of claim 1, wherein the optical system comprises two serially arranged optical lenses and a movement driver, at least one of the two serially arranged optical lenses being displaceable for varying the divergence of the laser beam on the optical transmission axis and coupled to the movement driver.

14. The ophthalmological device of claim 1, wherein the optical system comprises at least one from the following list: a spatial light modulator for modulating a wavefront of the pulsed laser beam, a surface light modulator for modulating reflection angles at a plurality of points of a reflection surface, a refraction modulator for modulating a refractive index of an optical element at a plurality of points in a cross section of a beam path of the pulsed laser beam, and an amplitude modulator for amplitude modulation at the plurality of points in the cross section of the beam path of the laser beam.

15. The ophthalmological device of claim 1, wherein the optical system comprises at least one optical element from the following list: a wedge plate, a prism, a lens, a diffractive optical element, and an aspherical mirror, the optical element being arranged adjustably in a beam path to the projection optical unit and configured to generate in the beam path a varying divergence of the laser beam dependent on a scanning angle of the scanning movement performed by the second scanner system along the scanning line.

16. The ophthalmological device of claim 1, wherein the second scanner system comprises at least one scanner from the following list: a resonant scanner, an oscillating scanner, a freely addressable scanner, a galvano-scanner, a piezo-driven scanner, a microelectro-mechanical scanner, an acousto-optical modulator scanner, and an electro-optical modulator scanner.

17. The ophthalmological device of claim 1, wherein the first scanner system comprises a mechanical scanner, the mechanical scanner comprising at least one movement driver configured to move the projection optical unit along the processing line.

18. The ophthalmological device of claim 1, wherein the first scanner system is arranged upstream of the projection optical unit and comprises a beam-deflecting scanner, the beam-deflecting scanner comprising at least one deflection mirror movable about an axis for deflecting the pulsed laser beam along the processing line.

19. The ophthalmological device of claim 1, wherein the optical system is arranged upstream of the first scanner system.

20. An apparatus comprising:
a first scanner system configured to scan eye tissue with a pulsed laser beam in an x-scanning direction and in a y-scanning direction, perpendicular to the x-scanning direction, to scan the eye tissue with the pulsed laser beam along a processing line transverse to a projection direction;
an optical system with an optical transmission axis, configured to generate a varying divergence of the pulsed laser beam, such that a focus is displaced in the projection direction;
a second scanner system disposed upstream of the first scanner system and configured for beam-deflecting scanning of the eye tissue with the pulsed laser beam in a scanning movement along a scanning line transverse to the optical transmission axis and superimposed on the processing line; and
a rotation element arranged downstream of the optical system and configured to rotate about the optical transmission axis a scanning plane defined by the optical transmission axis and the scanning movement of the second scanner system.

* * * * *